US006984977B2

(12) United States Patent
Wellstood et al.

(10) Patent No.: US 6,984,977 B2
(45) Date of Patent: Jan. 10, 2006

(54) SCANNING SQUID MICROSCOPE WITH IMPROVED SPATIAL RESOLUTION

(75) Inventors: Fred Wellstood, Lanham, MD (US); Erin Fleet, Alexandria, VA (US); Sojiphong Chatraphorn, Bankok (TH)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 10/416,489

(22) PCT Filed: Sep. 14, 2001

(86) PCT No.: PCT/US01/26024

§ 371 (c)(1),
(2), (4) Date: Oct. 28, 2003

(87) PCT Pub. No.: WO03/025603

PCT Pub. Date: Mar. 27, 2003

(65) Prior Publication Data

US 2004/0051524 A1 Mar. 18, 2004

(51) Int. Cl.
*G01R 33/02* (2006.01)

(52) U.S. Cl. ............................ 324/248; 326/5; 505/162
(58) Field of Classification Search ................ 324/248, 324/244, 228, 239, 249; 600/409; 326/5; 505/162; 327/366, 367, 370, 527, 528
See application file for complete search history.

(56) References Cited

U.S. PATENT DOCUMENTS

| 5,444,372 A | * | 8/1995 | Wikswo et al. ............. 324/248 |
| 5,491,411 A | | 2/1996 | Wellstood et al. |
| 5,786,690 A | | 7/1998 | Kirtley et al. |
| 5,894,220 A | | 4/1999 | Wellstood et al. |
| 5,986,280 A | * | 11/1999 | Kugai .......................... 257/34 |
| 6,025,713 A | | 2/2000 | Morooka et al. |
| 6,230,037 B1 | | 5/2001 | Tsukada et al. |
| 6,275,719 B1 | * | 8/2001 | Kandori et al. ............. 600/409 |
| 6,842,637 B2 | * | 1/2005 | Tsukada et al. ............. 600/409 |

FOREIGN PATENT DOCUMENTS

WO    WO 00/20879    4/2000

OTHER PUBLICATIONS

Keji Tsukada et al., Multichannel SQUID System Detecting Tangential Components of the Cardiac Magneitic Field, 1995, Rev. Sci. Instrum. 66 (10), pp. 5085-5091.*

(Continued)

*Primary Examiner*—Bot Ledynh
*Assistant Examiner*—Kenneth J. Whittington
(74) *Attorney, Agent, or Firm*—Rosenberg, Klein & Lee

(57) ABSTRACT

A scanning SQUID microscope for acquiring spatially resolved images of physical properties of an object includes a SQUID sensor arranged in perpendicular to the plane of the object under investigation for detecting tangential component of the magnetic field generated by the object. During scanning of the SQUID sensor over the object under investigation, the position signal from a position interpreting unit, as well as relevant output signals from the SQUID sensor are processed by a processing unit which derives from the data, spatially resolved images of the physical properties of the object. The specific orientation of the SQUID sensor with respect to the plane of the object permits an enlarged area of the SQUID chip on which the modulation and feedback line can be fabricated in the same technological process with the SQUID sensor. Additionally, larger contact pads afforded provide for lower contact resistance and ease in forming contact with bias and read-out wires.

13 Claims, 7 Drawing Sheets

OTHER PUBLICATIONS

E.F. Fleet et al., HTS Scanning SQUID Microscopy of Active Circuits, 1999, IEEE Transactions on Applied Superconductivity, vol. 9, No. 2, pp. 4103-4106.*

E.F. Fleet et al., Determination of Magnetic Properties Using a Room-Temperature Scanning SQUID Microscope, 2001, IEEE Transactions on Applied Superconductivity, vol. 11, No. 1, pp. 1180-1183.*

* cited by examiner

B-FIELD AVERAGED OVER
AREA OF A SQUID IN
THE DIRECTION OF A SCAN

SCANNING SQUID MICROSCOPE WITH IMPROVED SPATIAL RESOLUTION

This invention was made with the Government support under Contract Number MDA 904 99 C 2553 awarded by the National Security Agency. The Government has certain rights in the invention.

FIELD OF THE INVENTION

The present invention is directed to a magnetic scanning device such as a scanning SQUID (Superconducting Quantum Interference Device) microscope; and more particularly to an apparatus and technique for improving the spatial resolution of the scanning SQUID microscope.

Even more particularly, the present invention relates to a scanning SQUID microscope for acquiring spatially resolved images of physical properties of an object where a SQUID sensor is positioned substantially perpendicular to a test surface of the object under investigation and where the SQUID sensor detects a tangential component of the magnetic field generated by the object. In this manner the spatial resolution of the SQUID microscope is not limited to the area of the SQUID sensor.

BACKGROUND OF THE INVENTION

Scanning SQUID microscopes have been developed and used for acquiring spatially resolved images of physical properties of different objects by non-invasively measuring magnetic properties of materials and devices by means of superconducting quantum interference devices, also known as SQUID sensors. Prior magnetic imaging devices using SQUIDS have maintained spatial resolution on the scale of a millimeter or larger which is too large for microscopically resolving images needed in semiconductors/micro-electronics testing. Additionally, these devices also required placing samples in a vacuum. Some samples such as liquids or biological specimens cannot tolerate vacuum, thus it is not practical to measure sources of biomagnetism which are currently the focus of much of the existing low spatial resolution SQUID imaging.

U.S. Pat. No. 5,491,411 discloses methods and apparatus for imaging microscopic spatial variations in small currents and magnetic fields capable of providing measurements of magnetic fields with enhanced spatial resolution and magnetic field sensitivity. However, the device requires placing a sample within a dewar which may result in the unwanted destruction of the sample when it is exposed to cryogenic liquid or a vacuum. Arguendo, even if the sample is able to tolerate the vacuum environment or cryogenic medium, introducing the sample into the vacuum or cryogenic space for imaging is a somewhat cumbersome and time consuming task.

The problem was at least partially resolved by the apparatus for microscopic imaging of electrical and magnetic properties of a sample disclosed in U.S. Pat. No. 5,894,220. The device includes a housing having a first portion containing a cryogenic medium and a second portion enveloping a vacuum space. The cryogenic SQUID sensor is disposed within the vacuum space and in fluid communication with the cryogenic medium in the housing for heat exchange therewith. The sample for measurement is positioned outside of the housing, at room temperature or higher, and can be "seen" by the SQUID sensor through a thin window made in the wall of the housing. The output of the cryogenic SQUID sensor is monitored as it is scanned over the surface of the sample.

Another scanning SQUID microscope is described in the International Publication No. WO 00/20879. In this device, the SQUID sensor is scanned over the surface of the sample under study, particularly electronic circuit, and the measured data are subjected to spatial filtering and masking techniques in order to increase the spatial resolution and eliminate noise and edge artifacts in magnetic fields and electric field images of the sample.

In all scanning SQUID microscopes disclosed in the above-mentioned references the SQUID sensor loop is oriented to be in a plane parallel to the sample plane so that only the normal component $B_z$ of the detected magnetic field is measured. As shown in FIG. 1, SQUID chip 10 secured to the lowermost point of a sapphire tip 12 (attached to a tube 18) is disposed in parallel with the plane of a sample 14. As the sample 14 moves in perpendicular directions X and Y, the SQUID sensor detects the magnetic field generated by the sample 14. Particularly, as shown in FIG. 2, a magnetic field B is generated by a current path 16, extending in this particular example along the axis Y. The SQUID chip 10 disposed distance $Z_0$ from the current path 16, detects the normal component $B_z$ of the magnetic field B. The problem associated with this technique results from the fact that each acquired data point is the magnetic field averaged over the area of the SQUID sensor projection on the direction of a scan. Since, as shown in FIG. 3, the whole area of the SQUID sensor 10 faces (downwardly) toward the sample, and the projection area of the SQUID sensor onto the sample plane is large, the spatial resolution is then limited to the size of the SQUID sensor projecting onto the sample plane.

The scanning SQUID microscope described in the International Publication No. WO 00/20879, slightly improves the spatial resolution by processing the obtained data through filtering and masking electronics. This technique however requires excessive processing hardware and software and includes the limitations associated with parallel orientation of the SQUID sensor to the plane of the sample.

It is known in the prior art to operate SQUID sensors in a negative feedback loop or flux-locked loop. Referring again to FIG. 1, in order to couple magnetic flux into the SQUID sensor for maintaining a flux-locked loop, or for applying the read-out flux required for other imaging schemes, a three-turn coil 20 is wrapped around the sapphire tip 12. In order to increase the mutual inductance between the SQUID sensor and the coil 20 it was suggested in U.S. Pat. No. 5,894,220 to fabricate the coil directly on the SQUID chip using photolithographic printing technique known in the art. This suggestion is, however, more difficult in practice, since it requires a larger area of the SQUID that causes limitations associated with the trade-off between the spatial resolution and the size of the SQUID chip as discussed in previous paragraphs.

Further, SQUID bias and readout wires 22 are coupled between the SQUID chip 10 and the processing equipment 24. It is clear to those skilled in the art, that, as shown in FIG. 1, the contact between the wires 22 and the SQUID chip 10 is difficult to fabricate. Additionally, due to limitations applied to the size of the SQUID chip, the contact resistance to the device can be undesirably high if the contact pages are made too small.

It is therefore clear, that a different approach to the scanning SQUID microscope technique would be desirable to increase spatial resolution thereof without the necessity of using a rather complex processing technique as was proposed in the prior art. The subject system is directed to removing the limitations associated with the size of the SQUID and to afford a larger size of SQUID chip for accommodating modulation and feedback lines, as well as enlarged contact pads positioned thereon.

SUMMARY OF THE INVENTION

It is therefore an object of the present invention to provide a scanning SQUID microscope with enhanced spatial resolution.

It is another object of the present invention to provide a scanning SQUID microscope in which the spatial resolution is not limited by the size of the SQUID chip.

It is still a further object of the present invention to provide a scanning SQUID microscope in which the SQUID sensor is disposed in such a way that to achieve a negligible averaging of the detected magnetic field over the area of the SQUID chip in the scanning direction.

It is still another object of the present invention to provide a scanning SQUID microscope in which the SQUID sensor's plane is oriented substantially perpendicular to the sample plane in order that the projection area of the SQUID sensor onto the sample plane is negligible, and the spatial resolution is not limited to the size of the SQUID sensor.

It is a further object of the present invention to provide a scanning SQUID microscope which detects a tangential component of the magnetic field generated by the object under study due to its orientation substantially perpendicular to the plane of the object.

It is yet a further object of the present invention to provide a scanning SQUID microscope in which due to lack of the limitation of the size of the SQUID chip, the SQUID chip may be fabricated with dimensions which permit patterning the modulation and feedback line on the same chip with the SQUID sensor in the same technological process and also permits a convenient and low resistance coupling of the bias/read-out wires to the SQUID chip.

According to the teachings of the present invention, a scanning SQUID microscope for acquiring spatially resolved images of physical properties of an object takes advantage of a SQUID sensor oriented substantially perpendicular to the plane of the object under investigation. Specifically, the SQUID sensor is patterned on a substrate, the plane of which is positioned-in mutual perpendicular relationship with the surface under test containing the object. In this orientation, the projection area of the SQUID sensor onto the object plane is negligible, and the averaging of the detected signals over the area of the sensor in the scanning direction is negligibly small compared to conventional scanning SQUID microscopes where the whole area of the SQUID sensor faces in a downward orientation to the object under investigation. In this manner, the spatial resolution of the SQUID microscope of the present invention is not limited to the size of the SQUID sensor. It has been determined that, for example, at a separation between the SQUID sensor and the object, Z=150 microns, the spatial resolution obtained from the SQUID microscope of the present invention is about 40 microns and 20 microns for the sampling steps of 5 microns and 2 microns, respectively, while the spatial resolution obtained from the conventional SQUID microscope at the same object—SQUID sensor separation is about 80 microns.

During scanning of the object, the SQUID sensor detects magnetic field generated by the object at a plurality of positions and delivers a signal corresponding to the tangential component of the magnetic field detected.

The scanning SQUID microscope further includes a position interpreting unit for outputting a signal corresponding to a position where magnetic field readings are made. Imaging means are included which receive the signal from the position interpreting unit as well as the signal from the SQUID sensor corresponding to the tangential component of the magnetic field detected from which the imaging means further derive the spatially resolved images of the physical properties of the object.

The SQUID sensor is preferably formed of superconducting $YBa_2Cu_3O_7$ patterned on the substrate made of $SrTiO_3$ bicrystal., although other suitable materials known to those skilled in the art are also applicable. The SQUID sensor is attached to a cold-finger tip of the microscope and in particular to a flat or planar area extending at the end of the tip perpendicular relationship to the surface of the object under investigation. The tip is preferably made of sapphire., although other thermally conducting non-magnetic materials may be used.

The scanning SQUID microscope includes a housing which has a first section containing a cryogenic medium and a second section enveloping a vacuum space. A transparent window is formed in the second section of the housing for separating the vacuum space from the ambient atmosphere surrounding the housing. The cold-finger tip with the SQUID sensor attached thereto is positioned within the vacuum space, while the object under investigation is positioned in ambient surroundings and is separated from the SQUID sensor by the transparent window. A conduit extends between the first section of the housing and the sapphire tip to deliver the cryogenic medium to the sapphire tip for heat exchange with the SQUID sensor.

Means are provided in the scanning SQUID microscope for adjusting the relative disposition between the transparent window and the SQUID sensor as well as the distance between the SQUID sensor and the object under investigation.

Preferably, the object under investigation is positioned on a scanning stage capable of moving in horizontal X and Y directions mutually perpendicular each to the other, and in the Z direction perpendicular to both the X and Y directions.

With the SQUID chip oriented vertically, the size of the SQUID chip may be enlarged to permit larger contact areas for the wires coupling the SQUID chip to the processing means thus reducing the contact resistance to the SQUID. Additionally, due to the specific disposition of the SQUID chip at the sapphire tip it is much easier to connect the wires to the SQUID chip than known in the prior art.

It is important that due to the orientation of the SQUID chip, as well as the way it is attached to the sapphire tip of the SQUID microscope, a larger substrate area is permitted for the SQUID chip which also makes it easier to pattern the modulation and feedback line on the same substrate with the SQUID chip within the same technological process.

These and other novel features and advantages of the subject invention will be more fully understood from the following detailed description of the accompanying Drawings.

DESCRIPTION OF THE PREFERRED EMBODIMENTS

Figure 1:
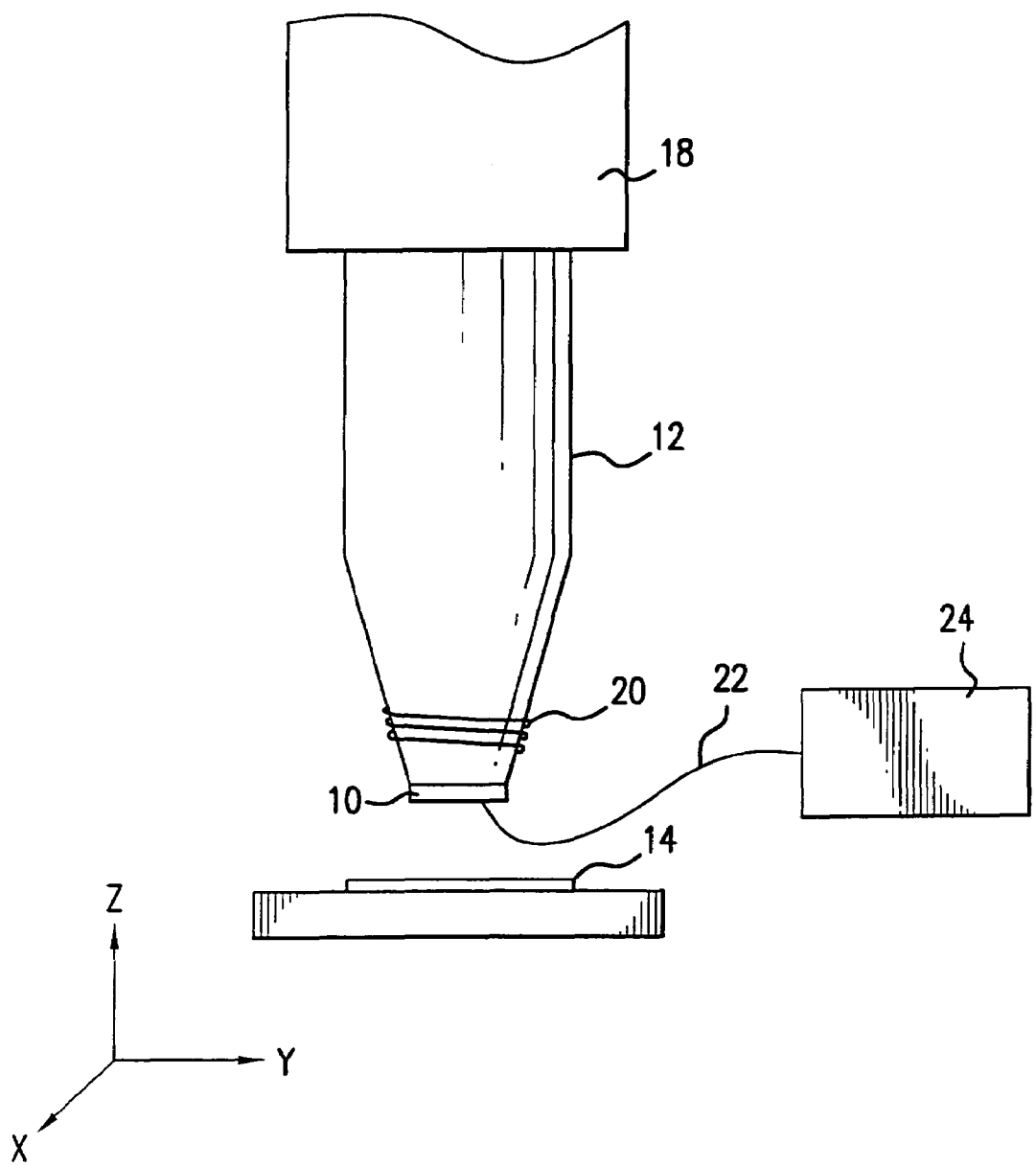
FIG. 1 is a schematic representation of a Z-SQUID microscope of the prior art.
Figure 2:
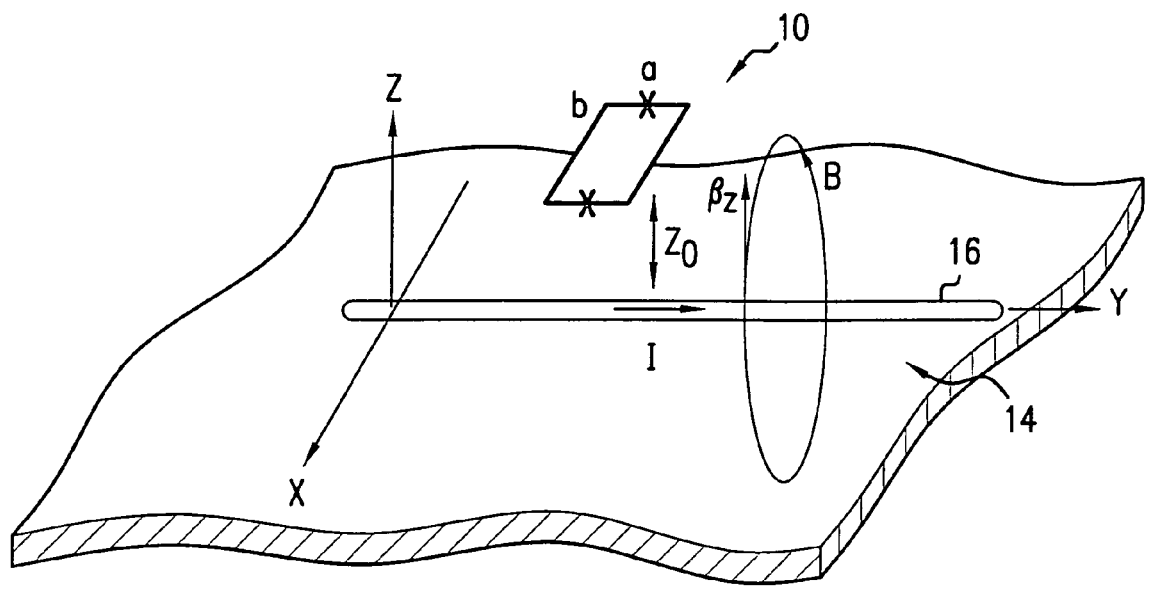
FIG. 2 is a schematic representation of the Z-SQUID sensor of the prior art oriented in parallel with regard to the scanning plane of an object under investigation.
Figure 3:
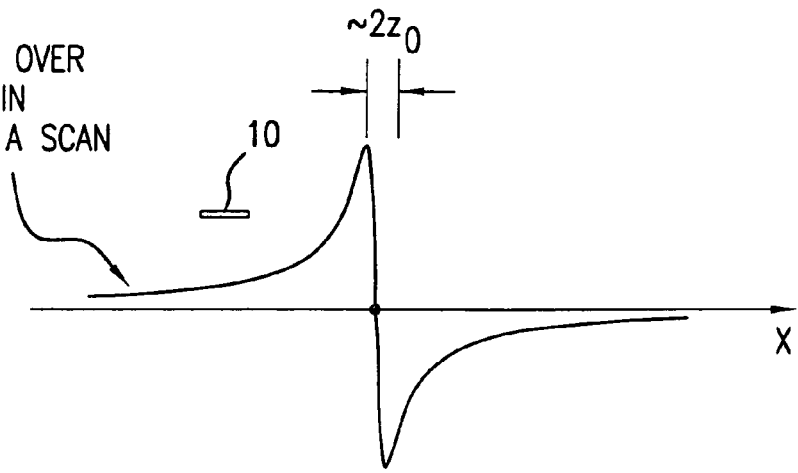
FIG. 3 is a diagrammatical representation of the magnetic field detected by the SQUID sensor of the prior art averaged over the area of the Z-SQUID in the direction of a scan.
Figure 4:
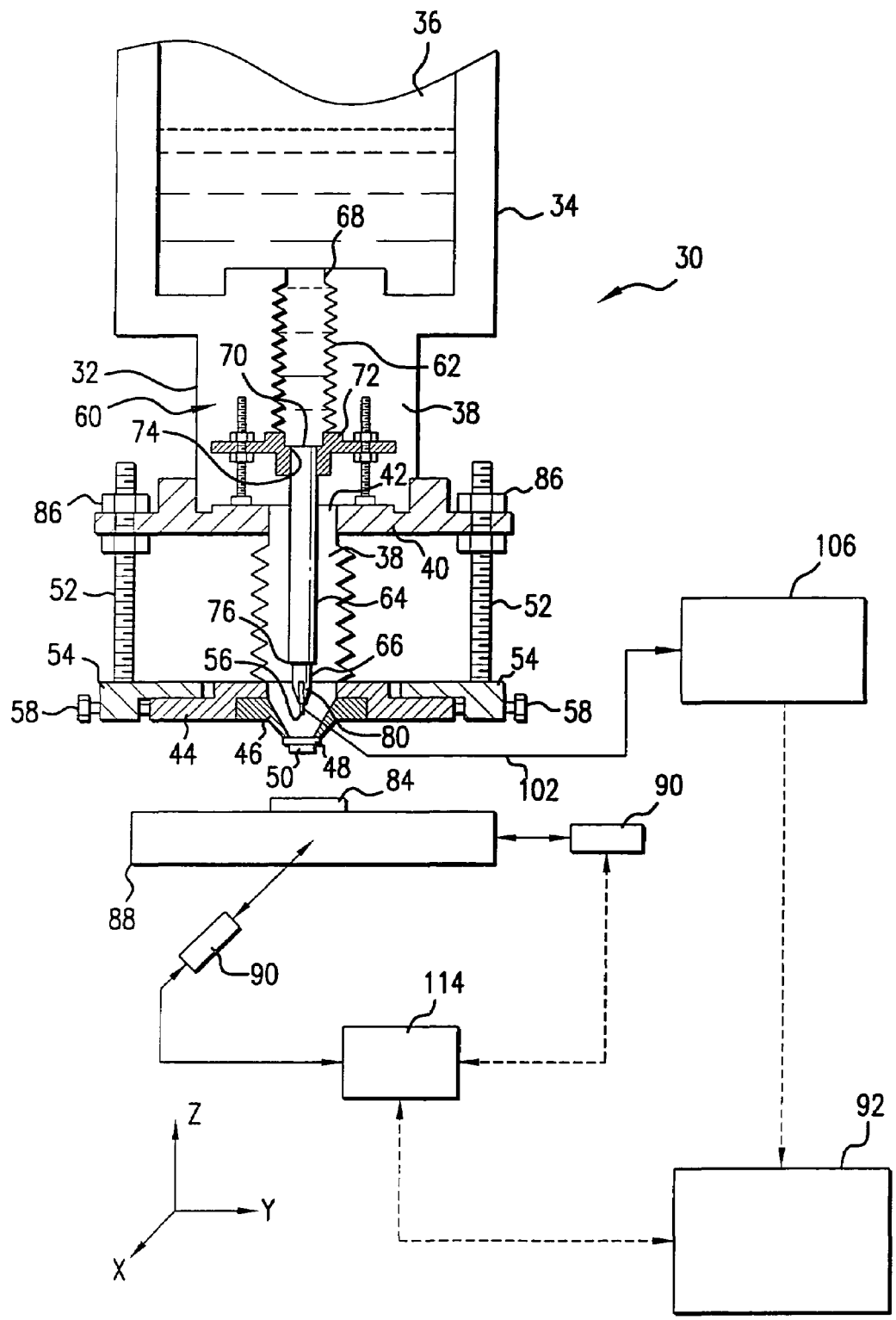
FIG. 4 shows a longitudinal section of the scanning SQUID microscope of the present invention.

Referring to FIG. 4, a scanning SQUID microscope 30 of the present invention includes a housing 32 which accommodates a cryogen containing portion 34 for receiving and holding liquid nitrogen 36, or any other cryogenic medium, as well as a vacuum space 38 which thermally insulates the cryogen containing portion 34 from room temperature. The housing 32 thus is a modified dewar assembly having the vacuum space 38 maintained at about $10^{-5}$ Torr. The housing 32 includes an annular plate 40 having a circular opening 42 located substantially in the center thereof. Spaced from the annular plate 40, is a window support 44 which supports a plastic flange 46 to the end of which a sapphire window support 48 is secured having an annular opening in which a transparent and thin window 50 is attached. The window 50 is preferably formed of sapphire and is approximately 25 microns thick.

The annular plate 40 is connected via three threaded rods 52 (only two of which are shown in FIG. 4) to a horizontal adjustment annular disk 54 to allow movement of the window 50 with respect to SQUID sensor 56. The adjustment screws 58 protrude through sides of the annular disk 54 to permit the movement of the window support 44 with respect to the annular disk 54 for alignment with the window 50 with respect to the SQUID sensor 56.

Figure 5:
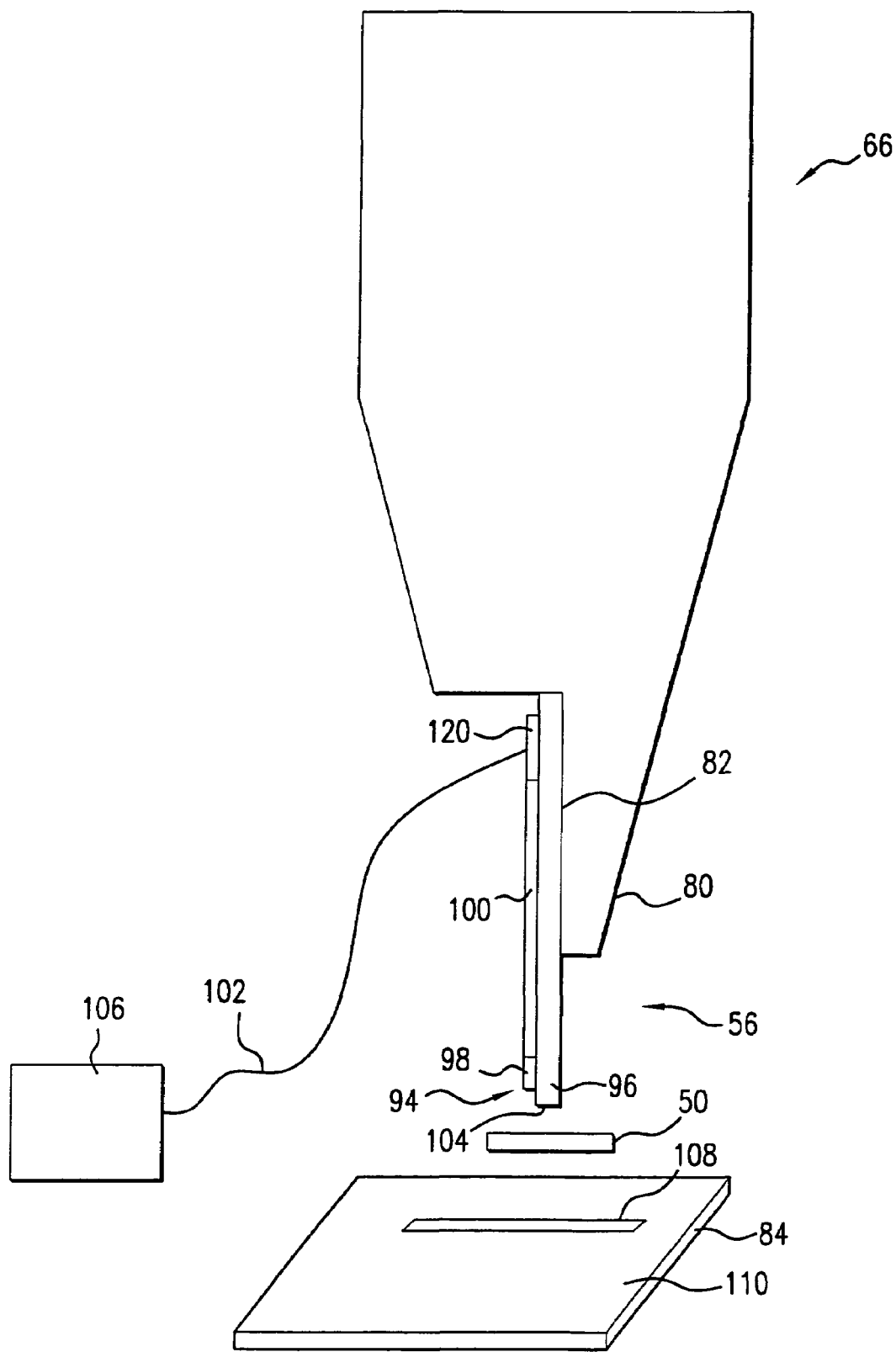
FIG. 5 is a schematic representation of the cold-finger sapphire tip of the scanning SQUID microscope of the present invention with the SQUID sensor attached thereto.

A flexible bellows tube 60 for delivery cryogen extends centrally and longitudinally within the housing 32 and includes stainless steel bellows 62 copper or brass tube 64 and a thermally conducting rod preferably forming a sapphire tip 66. The stainless steel bellows 62 is in open communication at the end 68 with the cryogen containing portion 34 of the housing 32. The end 70 of the bellows 62 is located in the vacuum space 38 and is mounted on the top of interior flange of a grommet 72. The end 74 of the tube 64 is seated and soldered on the bottom of the interior flange of the grommet 72 and thus is in open communication with the stainless steel bellows 62. The tube 64 extends through the vacuum space 38 of the housing 32 and further through the opening 42 in the annular plate 40. Located in the second end 76 of the tube 64 and fastened thereto with epoxy is the sapphire tip 66 which serves as a thermally conducting substrate for the SQUID chip 56. The end 80 of the sapphire tip 66 as best shown in FIG. 5, is fabricated with a flat or planar side surface 82 extending in parallel to the longitudinal axis of the sapphire tip 66. The SQUID chip 56 is adhesively attached to the flat side surface 82 and is securely maintained thereon during the operation of the scanning SQUID microscope 30.

Referring once again to FIG. 4, the cryogenic medium 36 from the cryogen containing portion 34 is supplied to the sapphire tip 66 through the stainless steel bellows 62 and the tube 64 to permit heat exchange between the SQUID chip and the liquid nitrogen.

The distance between the SQUID chip and the window 50 may be as great as 2–3 millimeters or they may be contiguous in relation to each other. The construction of the scanning SQUID microscope 30 permits maintenance of the SQUID chip temperature at 77° K while allowing for minute separation between the SQUID chip 56 and a room temperature sample 84, also referred herein as the object under investigation.

When the cryogenic liquid passes through the stainless steel bellows 62, and the copper tube 64 these elements may contract. However, such deformation will not prevent the position of the sapphire tip 66, nor the SQUID chip 56 from being close to the window, due to the fact that the window position can be vertically adjusted by means of the adjustment nuts 86.

The sample 84 is positioned outside of the housing 32 of the scanning SQUID microscope 30 on a scanning stage 88 schematically shown in FIG. 4 which is capable of movement in the three mutually perpendicular directions X, Y and Z. Preferably, the stage is motorized and provides positioning accuracy of about one micron or better. The scanning stage 88 and mechanism moving such is known to those skilled in the art and is not described herein in detail. The stage 88 is moved by the stepper motors 90 for driving the stage 88 in X and Y directions. It is preferable to mount the motors 90 as far as possible from the SQUID sensor (about 50 cm) and to envelop them in an eddy-current magnetic shield in order to shield the SQUID sensor from undesirable magnetic fields produced by the motors 90. The motors 90 are mechanically coupled to micrometers. The motors 90 are magnetically noisy, however, stepper motors and micrometers are used since they provide sufficient positioning accuracy.

Preferably, a computer or processor 92 with controlling software and peripherals for operating the motors is used to operate the scanning stage 88 in the scanning SQUID microscope of the present invention.

Figure 8:
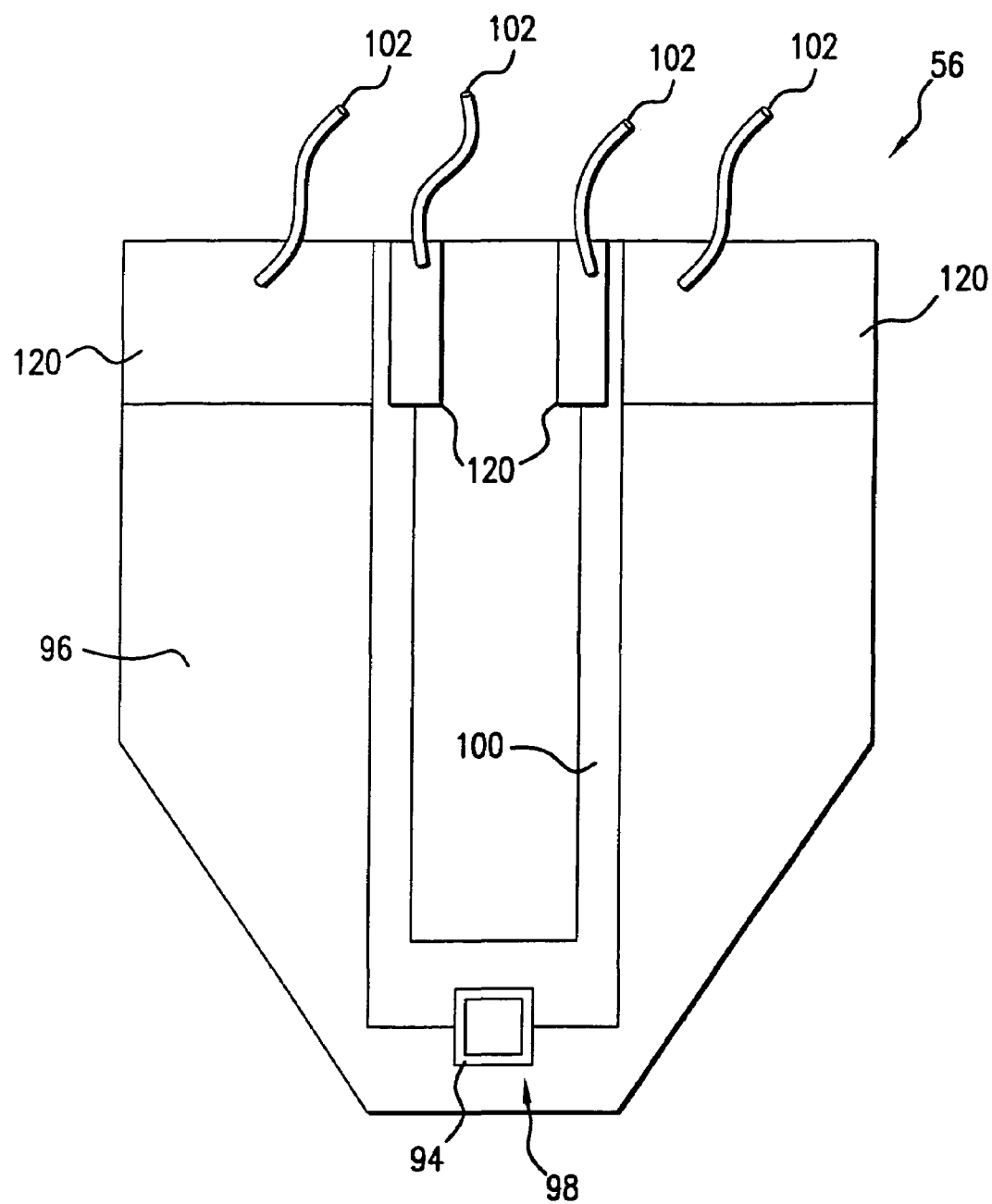
FIG. 8 is a planar view of the surface of the SQUID chip on which the SQUID sensor and modulation/feedback line are patterned in the same technological process.

In greater detail, the thermally conducting sapphire tip 66 may be approximately 1" long with a 0.25" diameter. The SQUID chip 56 may consist of a single 200 nm thick layer 94 of $YBa_2Cu_3O_7$ patterned on a 500 micron thick $SrTiO_3$ bi-crystal substrate 96, as best shown in FIGS. 5 and 8. The SQUID sensor 98 has a generally rectangular shape with the inner hole having widths approximating 10 microns and heights approximately 40 microns and with the outer approximate dimensions having widths of 30 microns and heights of 60 microns.

The modulation and flux feedback line 100 is patterned near the SQUID sensor 98 on the same substrate 96 using photolithographic printing techniques known in the art. After the patterns of the SQUID sensor 98 and modulation and feedback line 100 are formed on the substrate 96, the substrate 96 is cut into substantially rectangular pieces with the dimensions about 1.5 mm wide and 5 mm long. The SQUID chip 56, is glued to the sapphire tip 66 with the substrate 96 affixed to the flat side surface 82, as best shown in FIG. 5. After the epoxy is cured the end 104 of the SQUID chip 56 is polished down to about 800 microns width or smaller in order that the sapphire tip 66 can be mounted into the window 50. During this process, the end 104 of the SQUID chip is polished back, so that the SQUID is as close as possible to the end of the chip, preferably within a few microns.

Fabrication of the modulation and feedback line 100 directly on the SQUID chip provides an increased mutual inductance between the SQUID sensor 98 and line 100 thus enhancing the magnetic flux coupling into the SQUID for maintaining a flux-locked loop or for applying the read-out flux required for imaging circuitries of the scanning SQUID microscope of the present invention. It is clear to those skilled in the art that since the substrate 96 is large enough (1.5 mm×5 mm) the area thereon devoid of the SQUID sensor 98 and modulation and feedback line 100 constitutes a large enough area to provide larger contact areas 120 that makes the contact with bias and read-out wiring 102 easier and substantially reduces the contact resistance of the device.

Referring again to FIG. 4, when setting up the microscope for imaging, the window 50 and the end 104 of the substrate 96 are aligned by moving the window 50 by means of the adjusting nuts 86 or screws 58. Once the window 50 is leveled with respect to the SQUID, chip 56, the sample 84 on the scanning stage 88 is leveled with respect to the window 50 to insure that the separation between the sample and the SQUID sensor does not change during the scan as well as for achieving a small separation between the sample and the SQUID sensor. This operation is performed by moving the stage 88 in the Z direction shown in FIG. 4, either manually or automatically under the control of the computer 92. This operation is known to those skilled in the art and is not intended to be discussed in detail herein.

To obtain an image of the physical properties of the sample 84, individual raster scan lines are acquired by scanning the sample with the SQUID sensor in, for example, the X direction while simultaneously recording in the computer 92 the X coordinates (read from the motor-control board 114) and the relevant magnetic field measured (read from the SQUID read-out electronics 106). The process is further repeated for the sequence of Y values, by scanning the sample in the Y direction to construct a 2-dimensional image of the surface of the sample 84.

Figure 6:
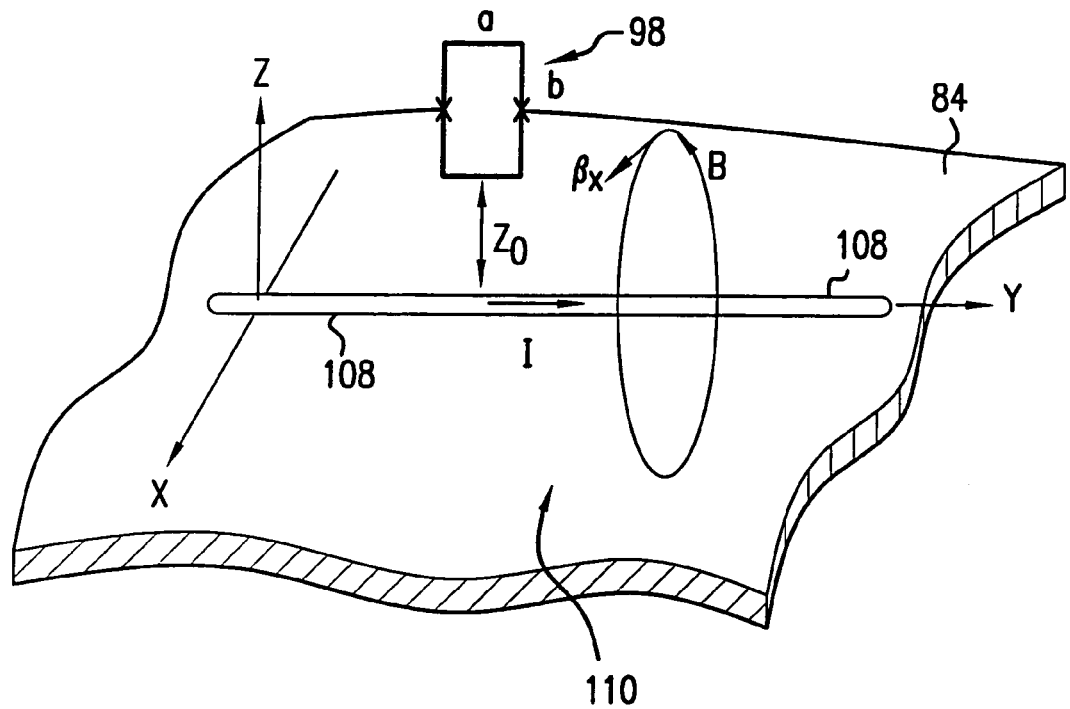
FIG. 6 shows schematically the relative disposition between the plane of the SQUID sensor of the present invention to the object under investigation.
Figure 7:
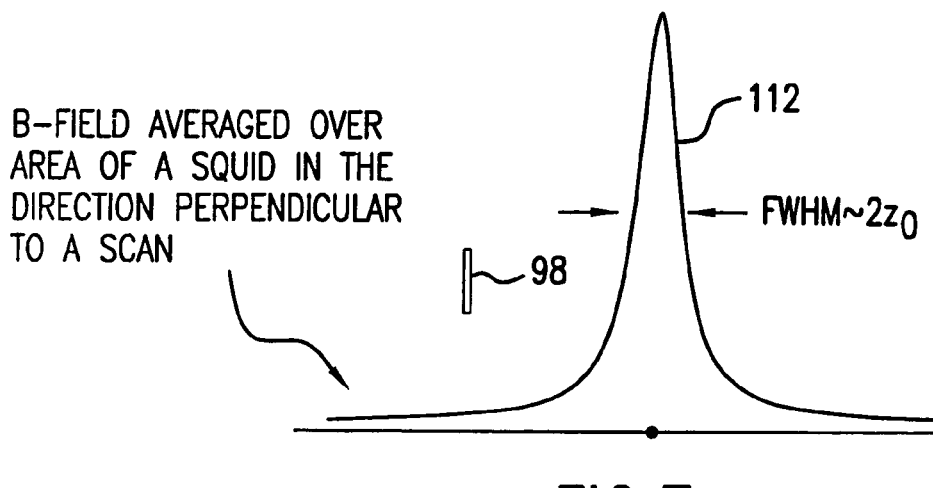
FIG. 7 is a diagrammatical representation of the detected magnetic field averaged over the area of the SQUID sensor projected onto the direction of a scan.

For example, as shown in FIG. 6, in the case when the sample 84 is a microelectronic circuitry having a current path 108 the current I flowing along the current path 108 generates a magnetic field B. The SQUID chip 56 having its substrate thereof oriented perpendicularly to the X-Y plane (scanning plane) is positioned a distance $Z_0$ from the surface 110 of the sample 84 and is scanned first in the X direction and then in the Y direction along the surface 110. During the scan, the SQUID sensor detects the tangential component $B_x$ of the magnetic field B as opposed to detection of normal component $B_z$ of the magnetic field generated by the sample in the scanning SQUID microscopes of the prior art. The spatial resolution of the scanning SQUID microscope depends on the detected magnetic field averaged over the area of a SQUID sensor projecting onto the sample plane. As best shown in FIGS. 7 and 5, the projection of the SQUID sensor 98 on the sample surface 110 is negligible and is determined only by the thickness of the layer of $YBa_2Cu_3O_7$ deposited onto the substrate 96 of the SQUID chip which is approximately 200 nanometers. Therefore, the spatial resolution in the scanning SQUID microscope of the present invention is substantially independent of the size of a SQUID chip which permits taking advantage of a substantially larger area of the SQUID chip, such as 1.5 mm×5 mm, as opposed to the SQUID chip of the prior art. Due to the substantially larger area of the SQUID chip it is possible to fabricate the modulation-and-feedback line 100 on the same chip as the SQUID sensor 98. It is also possible to fabricate larger contact pads 120 on the substrate 96, thus reducing the contact resistance of the device and making the contact with the bias and read-out wires 102 easier to implement.

FIG. 7 shows the current density—squared vs. X values in the X direction of scanning when the SQUID sensor scans the sample in the X direction. The spatial resolution is defined as the "whole width at half maximum" (FWHM) of the current density squared peak 112 generated by the current I flowing through the current path 108. As will be discussed in further paragraphs, the spatial resolution of the scanning SQUID microscope of the present invention defined as shown in FIG. 7 is higher than the spatial resolution of the conventional scanning SQUID microscope using the SQUID chips oriented in parallel to the sample plane.

Referring again to FIG. 4, during the acquisition of the images of physical properties of the sample 84, the position of the scanning stage 88 is determined by reading positions of the stepper motors 90. The control program of the computer 92 can read the stepper motor positions directly from a motor controller board 114 which may be mounted in the computer 92. Simultaneously, the read-out electronics 106 acquires data from the SQUID sensor 98.

Both the SQUID output and the position of the stage 88 are converted into digital form and recorded in the computer 92. Once data has been acquired using a control program of the computer 92, it is converted into an image. In its raw form, the image data consists of a set of N line scans (Y values) intersected with M line scans (X values), with one or more associated magnetic field values at each of the N×M points. To provide an image, the data is first spatially regularized, i.e., linearly interpolated into rectangular space grids. Then an image rendering program is used to assign a level of gray to each grid point. The control program is well-known in the art and is not discussed in further detail. The control program processes the received position signals from the motor controller 114, in synchronism with outputs of SQUID sensor read by the read-out electronics 106 and derives therefrom the spatially resolved images of the physical properties of the object, such as for example magnetic fields emanating from the surface of the sample 84, etc.

Figure 9:
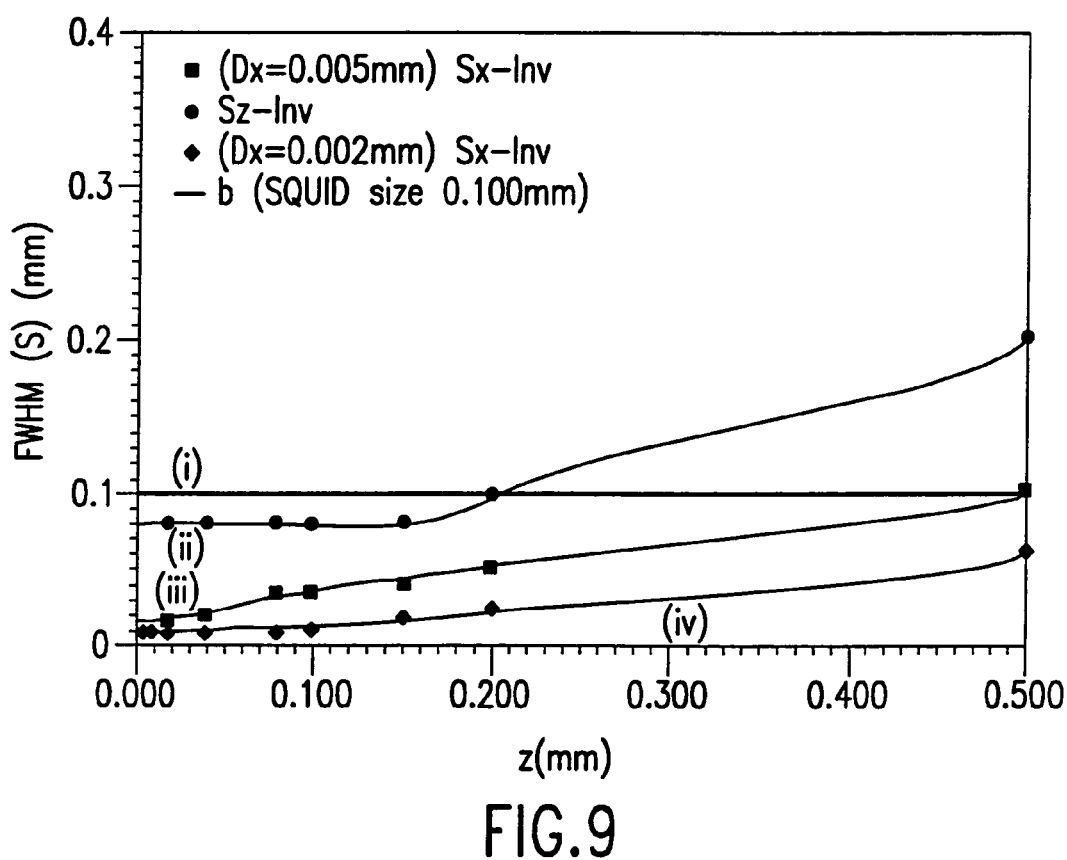
FIG. 9 is a diagram presenting comparison between the spatial resolutions of the scanning SQUID microscope of the prior art and of the present invention.

Calculations and simulations showing that the spatial resolution obtained with the SQUID microscope of the present invention is not restricted to the size of the SQUID chip have been completed. The chart in FIG. 9 shows the comparison of spatial resolution obtained from the SQUID microscope of prior art and the SQUID microscope of the present invention. In the chart, the spatial resolution obtained after applying a magnetic inverse technique, discussed in following paragraphs, is plotted vs. the sample to SQUID separation. The spatial resolution is defined as the "full width at half maximum" (FWHM) of the current-density-squared peak generated by a current flowing through the wire 108 of the sample 84, as shown in FIG. 6.

In FIG. 9, trace i (horizontal line) corresponds to the spatial resolution of the SQUID sensor with the side dimension~100 microns. Trace ii shows the spatial resolution from the SQUID microscope of the prior art with data sampling step of 5 microns. It is shown that for the prior art, the spatial resolution is limited to about 80 microns and is limited by the 100 micron size of the SQUID sensor even when the sample to SQUID separation is reduced to 20 microns. Traces iii and iv show the spatial resolution for the SQUID microscope of the present invention with data sampling steps of 5 microns and 2 microns, respectively. The spatial resolution in the X-direction in these two traces is not limited by the size of the SQUID. For example, at a separation Z=150 microns, the spatial resolution obtained from the SQUID microscope of the present invention is 40 microns and 20 microns for the sampling steps of 5 microns and 2 microns respectively, as compared with the spatial resolution obtained from the SQUID microscope of the prior art which is about 80 microns.

To obtain data plotted in FIG. 9, a magnetic inversion technique was applied which permits extraction of the current path from the magnetic field data obtained with the SQUID sensors. The principles of the magnetic inversion technique is based on the Biot-Savart Law, which relates current density to magnetic field. The two main magnetic inversion techniques are directed to the application of a Fourier transform and spatial filtering to the measured magnetic field. The reduction of noise and the edge effect of the data can be eliminated by using an appropriate signal processing filter such as that disclosed in the International Publication #WO 00/20879.

In the magnetic inversion technique, it is assumed that the current paths are confined in a sheet of thickness d which is much smaller than the SQUID-sample separation z. From the Biot-Savart Law, $B_z=(x,y,z)$ and $B_x(x,y,z)$ are written as follows:

$$B_z(x, y, z) \approx \frac{\mu_0 d}{4\pi} \int\int \frac{J_x(x', y') \cdot (y - y') - J_y(x', y') \cdot (x - x')}{[(x - x')^2 + (y - y')^2 + z^2]^{3/2}} dx' dy' \quad (1)$$

$$B_x(x, y, z) \approx \frac{\mu_0 d}{4\pi} z \int\int \frac{J_x(x', y')}{[(x - x')^2 + (y - y')^2 + z^2]^{3/2}} dx' dy' \quad (2)$$

where $\mu_0$ is the permeability of free space, $J_x$ and $J_y$ are x and y components of current density, respectively.

The convolution theorem allows Eqs. (1) and (2) to be written in Fourier space as:

$$B_z(k_x, k_y, z) = \frac{i\mu_0 d}{2} \frac{e^{-KZ}}{k} [k_y \cdot j_x(k_x, k_y) - k_x \cdot j_y(k_x, k_y)] \quad (3)$$

$$b_x(k_x, k_y, z) = \frac{\mu_0 d}{2} e^{-KZ} j_y(k_x, k_y) \quad (4)$$

where $b_z(k_x,k_y,z)$, $j_x(k_x,k_y)$ and $j_y(k_x,k_y)$ are the two-dimensional Fourier transforms of the magnetic field and the current density, respectively. The $k_x$ and $k_y$ are the components of the spatial frequency vector k.

In the case of the SQUID microscope of the prior art, the z-component of the magnetic field $B(x,y,z)$ is detected, therefore $b_z(k_x,k_y,z)$ is the Fourier transform of the data obtained from the prior SQUID microscope. In Eq. (3), $j_x(k_x,k_y)$ and $j_y(k_x,k_y)$ are unknowns. However, using the conservation of current density, an additional equation is obtained which allows us to write $j_x(k_x,k_y)$ and $j_y(k_x,k_y)$ in terms of $b_z(k_x,k_y,z)$:

$$j_z(k_x, k_y, z) = -\frac{i2}{\mu_0 d} e^{KZ} \frac{k_y}{k} b_z(k_x, k_y, z), \quad (5)$$

$$j_y(k_x, k_y, z) = \frac{i2}{\mu_0 d} e^{KZ} \frac{k_x}{k} b_z(k_x, k_y, z). \quad (6)$$

The signal processing filters can be applied to the Eqs. (5) and (6) to eliminate undesired noise and edge effect of the data. Taking an inverse Fourier the current-density-squared is found which is the sum of each squared component.

In the case of X-SQUID microscope of the present invention, the x-component of the magnetic field $B_x(x,y,z)$ is detected, therefore, $b_z(k_x,k_y,z)$ is the Fourier transform of the data obtained from the X-SQUID. Eq. (4) is less complicated than Eq. (3) since it has only one unknown, $j_y(k_x,k_y)$. Then $j_y(k_x,k_y)$ in terms of $b_x(k_x,k_y)$ is written:

$$j_y(k_x, k_y, z) = \frac{2}{\mu_0 d} e^{KZ} b_x(k_x, k_y, z). \quad (7)$$

Signal processing filters can be also applied to Eq. (7) to eliminate undesired noise and edge effects of the data. Specifically from Eq. (2), only the y-component of the current density generates $B_x(x,y,z)$, so the signal from the Fourier transform in Eq. (7) will be mostly along $k_x$-direction. The appropriate signal processing filter, therefore, maintains the signal along the $k_x$-direction and eliminates the off-$k_x$-axis signals which are mostly noise. The Inverse Fourier transform of filtered Eq. (7) permits the obtaining of $J_y(x,y)$. Note that current-density-squared is the square of $J_y(x,y)$ for the X-SQUID.

The above analysis assumes that the SQUID is a point sensor so that the magnetic flux linked into the SQUID is just due to the field at one position (x,y,z). However, any real SQUID has a non-zero pickup lop area over which the magnetic field must be integrated to get the total flux in the SQUID loop. This integration is essentially a process that results in the SQUID output being proportional to the average field over the area of the SQUID loop. In the case of proportional to the average field over the area of the SQUID loop. In the case of the z-SQUID, this averaging causes blurring of the current sources that is not removed by the above magnetic inverse technique. In the case of an x-SQUID, however the effect of the blurring due to averaging over the body of the SQUID can be removed in the x-direction by replacing Equation (7) above with the relation:

$$j_y(k_x,k_y,z) = 2k/[\mu_0(e^{kz}-1)]e^{-k(z+h)} b_x(k_x,k_y,x) \quad (8)$$

where $b_x(k_x,k_y,z)$ is the Fourier transform of the magnetic field averaged over the SQUID loop (which is directly related to the output of the SQUID feedback output), h is the height of the SQUID loop in the z-direction, and z is the vertical distance between the current carrying region and the closest edge of the SQUID. It is the existence of the relationship (8) for the x-SQUID which ultimately allows for the production of current density images with spatial resolution that are not completely limited by the SQUID size, as is the case for SQUIDs oriented in the z-direction.

It is therefore clear that due to the orientation of the SQUID sensor substantially perpendicular to the plane of the sample under the investigation, the enhanced spatial resolution of the imaging is attained wherein the spatial resolution is not limited to the size of the SQUID chip. Due to the new structure of the scanning SQUID microscope, not only an increased spatial resolution is obtained, but improvement to the SQUID sensor itself can be found by fabricating modulation and feedback lines directly on the same substrate with the SQUID sensor in one technological process, thus increasing the mutual inductance between the SQUID sensor and the modulation and feedback lines, as well as simplifying the design of the overall scanning SQUID microscope. Due to the larger area of the SQUID chip, the enlarged contact pads provide for reduced contact resistance of the device as well as simplifying the coupling of the bias and read-out wires to the SQUID chip.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases particular locations of elements may be reversed or interposed, all without departing from the spirit or scope of the invention as defined in the appended claims.

What is claimed is:

1. A scanning SQUID microscope for acquiring spatially resolved images of physical properties of an object, comprising:
    a SQUID sensor patterned on a substrate arranged substantially perpendicular to at least one surface under the test, said object being mounted on said surface, said SQUID sensor having a SQUID loop;
    said SQUID sensor detecting the tangential component $B_x$ of a magnetic field generated by said object in at least one relative position in said at least one surface under the test and generating an output signal corresponding to the magnetic field detected at said relative position; and
    a computational unit calculating current density $j_y(k_x,k_y,z)$ as:

$$j_y(k_x,k_y,z)=2k/[\mu_0(e^{kz}-1)]e^{-k(z+h)}b_x(k_x,k_y,z)$$

where $b_x(k_x,k_y,z)$ is the Fourier transform of the magnetic field averaged over the SQUID loop,
        h is a height of the SQUID loop in the z-direction, and z is the vertical distance between said at least one surface under the test and an edge of the SQUID closest thereto.

2. The scanning SQUID microscope of claim 1, wherein said computational unit converts said output signal data to current density data, said computational unit including means for providing current density images independent of the dimensions of the SQUID sensor.

3. The scanning SQUID microscope of claim 1, wherein said object includes a microelectronic circuit, and wherein said surface under the test includes at least one current path generating the magnetic field.

4. The scanning SQUID microscope of claim 1, further comprising:
    (a) position interpreting means for outputting a position signal corresponding to said at least one relative position; and
    (b) imaging means for receiving said position signal from said position interpreting means, receiving said output signal from said SQUID sensor, and deriving therefrom the spatially resolved images of the physical properties of said object.

5. The scanning SQUID microscope of claim 1, further comprising:
    a scanning stage carrying said object thereon, and
    means for relocating said object along with said scanning stage in at least first and second mutually perpendicular directions forming a scanning plane extending substantially perpendicular to said substrate of said SQUID sensor.

6. The scanning SQUID microscope of claim 1, further comprising means for adjusting distance between said SQUID sensor and said at least one surface under the test of said object.

7. The scanning microscope of claim 1, further comprising modulation/feedback line patterned on said substrate.

8. The scanning SQUID microscope of claim 1, wherein said SQUID sensor is formed of superconducting $YBa_2CU_3O_7$, and wherein said substrate is made of $SrTiO_3$.

9. The scanning SQUID microscope of claim 1, further comprising:
    a heat conducting tip including a substantially flat area extending substantially perpendicular to said surface under the test of said object, said SQUID sensor being secured to said flat area of said heat conducting tip.

10. The scanning SQUID microscope of claim 9, further comprising:
    a housing including a first section containing a cryogenic medium, and a second section enveloping a vacuum space;
    a transparent window formed in said second section of said housing and separating said vacuum space from said object disposed in ambient atmosphere surrounding said housing, said heat conducting tip with said SQUID sensor secured thereto being disposed in said second section of said housing adjacent to said transparent window;
    a conduit extending between said first section of said housing and said heat conducting tip to deliver said cryogenic medium thereto for heat exchange with said SQUID sensor; and
    means for adjusting the relative disposition between said transparent window and said SQUID sensor.

11. A method for acquiring spatially resolved images of physical properties of an object generating magnetic field, comprising the steps of:
    positioning the object on a scanning stage,
    arranging a SQUID sensor substantially in mutually perpendicular relationship between the plane thereof and a surface under the test of said object, said SQUID sensor having a SQUID loop,
    scanning said surface under the test of said object with said substantially perpendicularly oriented thereto SQUID sensor to detect a tangential component $B_x$ of the magnetic field generated by said object at a plurality of locations of said surface under the test of said object,
    processing outputs of said SQUID sensor corresponding to the $B_x$ magnetic field detected at said plurality of locations in combination with respective position signals corresponding to said locations, and
    deriving therefrom the spatially resolved images $j_y(k_x,k_y,z)$ of the physical properties of said object as:

$$j_y(k_x,k_y,z)=2k/[\mu_0(e^{kz}-1)]e^{-k(z+h)}b_x(k_x,k_y,z)$$

where $b_x(k_x,k_y,z)$ is the Fourier transform of the magnetic field averaged over the SQUID loop,
        h is a height of the SQUID loop in the z-direction, and z is the vertical distance between the surface under the test and an edge of the SQUID closest thereto.

12. The method of claim 11, further comprising the step of:
    adjusting distance between said SQUID sensor and said object.

13. The method of claim 12, further comprising the steps of:
    patterning said SQUID sensor on a substrate, and
    patterning a modulation/feedback line on said substrate substantially simultaneously with said SQUID sensor.

* * * * *